US012630858B2

(12) United States Patent
Ishimaru et al.

(10) Patent No.: US 12,630,858 B2
(45) Date of Patent: May 19, 2026

(54) CELL DETECTION DEVICE AND CELL DETECTION METHOD

(71) Applicant: Hitachi High-Tech Corporation, Tokyo (JP)

(72) Inventors: Masako Ishimaru, Tokyo (JP); Hideyuki Noda, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 1040 days.

(21) Appl. No.: 17/425,993

(22) PCT Filed: Oct. 11, 2019

(86) PCT No.: PCT/JP2019/040147
§ 371 (c)(1),
(2) Date: Jul. 27, 2021

(87) PCT Pub. No.: WO2020/166130
PCT Pub. Date: Aug. 20, 2020

(65) Prior Publication Data
US 2022/0154245 A1 May 19, 2022

(30) Foreign Application Priority Data

Feb. 15, 2019 (JP) ................................. 2019-025209

(51) Int. Cl.
*C12Q 1/66* (2006.01)
*B01L 3/00* (2006.01)
(Continued)

(52) U.S. Cl.
CPC .......... *C12Q 1/66* (2013.01); *B01L 3/502715* (2013.01); *B01L 3/50825* (2013.01);
(Continued)

(58) Field of Classification Search
CPC ... C12Q 1/66; C12Q 1/04; C12Q 1/22; C12Q 1/06; B01L 3/502715; B01L 3/50825;
(Continued)

(56) References Cited

U.S. PATENT DOCUMENTS

| | | | |
|---|---|---|---|
| 6,074,870 A | 6/2000 | Berndt | |
| 2009/0183555 A1* | 7/2009 | Meng ................ | B01L 3/502715 |
| | | | 427/58 |

(Continued)

FOREIGN PATENT DOCUMENTS

| | | |
|---|---|---|
| JP | 2696081 B2 | 1/1998 |
| JP | 2001170 A | 1/2001 |

(Continued)

OTHER PUBLICATIONS

Search Report mailed Sep. 16, 2022 in European Application No. 19914710.9.

(Continued)

*Primary Examiner* — Charles Capozzi
*Assistant Examiner* — Jacqueline Brazin
(74) *Attorney, Agent, or Firm* — Miles & Stockbridge, P.C.

(57) ABSTRACT

A cell detection device that detects a cell in a specimen with high sensitivity and includes a sealed container having a sealable specimen introduction portion, a culture portion that holds a culture solution, an extraction reagent portion that holds an extraction reagent, and a luminescent reagent portion that holds a luminescent reagent, a contact mechanism that controls contact between the culture solution, the extraction reagent, and the luminescent reagent, a photodetector that detects luminescence from the luminescent reagent portion, and a calculator that determines growth of a cell based on a detection signal of the photodetector. The culture solution, the extraction reagent, and the luminescent (Continued)

reagent are separately disposed in the sealed container, and the contact mechanism brings the culture solution to which a specimen is added and the extraction reagent into contact to obtain an extraction solution, and intermittently brings the extraction solution and the luminescent reagent into contact.

13 Claims, 6 Drawing Sheets

(51) Int. Cl.

| | |
|---|---|
| *C12M 1/06* | (2006.01) |
| *C12M 1/26* | (2006.01) |
| *C12M 1/34* | (2006.01) |
| *C12Q 1/04* | (2006.01) |
| *C12Q 1/22* | (2006.01) |
| *G01N 21/64* | (2006.01) |

(52) U.S. Cl.

CPC ............ *C12M 27/02* (2013.01); *C12M 33/04* (2013.01); *C12M 41/12* (2013.01); *C12Q 1/04* (2013.01); *C12Q 1/22* (2013.01); *G01N 21/6428* (2013.01); *B01L 2200/16* (2013.01); *B01L 2300/042* (2013.01); *B01L 2300/044* (2013.01); *B01L 2300/0654* (2013.01); *B01L 2400/0478* (2013.01)

(58) Field of Classification Search

CPC ........... B01L 2200/16; B01L 2300/042; B01L 2300/044; B01L 2300/0654; B01L 2400/0478; B01L 3/0241; B01L 3/502; C12M 27/02; C12M 33/04; C12M 41/12; G01N 21/6428; G01N 15/01; G01N 15/075; G01N 2015/0681; G01N 2015/0687; G01N 15/06; G01N 21/763

USPC ...................................................... 435/287.1

See application file for complete search history.

(56) References Cited

U.S. PATENT DOCUMENTS

| | | | |
|---|---|---|---|
| 2012/0082977 A1 | 4/2012 | Rajagopal et al. | |
| 2018/0057853 A1 | 3/2018 | Noda et al. | |

FOREIGN PATENT DOCUMENTS

| | | | |
|---|---|---|---|
| JP | 2004313028 A | 11/2004 | |
| WO | 2000065022 A1 | 11/2000 | |
| WO | WO-2016147313 A1 * | 9/2016 | .............. C12M 1/34 |

OTHER PUBLICATIONS

Search Report mailed Dec. 17, 2019 in International Application No. PCT/JP2019/040147.

Written Opinion mailed Dec. 17, 2019 in International Application No. PCT/JP2019/040147.

Ming-Cheng Wang et al. "Early identification of microorganisms in blood culture prior to the detection of a positive signal in the BACTEC FX system using matrix-assisted laser desorption/ionizationetime of flight mass spectrometry" Journal of Microbiology, Immunology and Infection, Oct. 2015, pp. 419-424, vol. 48.

International Preliminary Report on Patentablity mailed Jul. 29, 2019 in International Application No. PCT/JP2019/040147.

* cited by examiner

CELL DETECTION DEVICE AND CELL DETECTION METHOD

TECHNICAL FIELD

The present disclosure relates to a cell detection device and a cell detection method.

BACKGROUND ART

In order to check whether or not microbes are present in a normally sterile specimen such as a clinical specimen such as blood or a cell preparation, a method of adding a specimen to a liquid culture medium for cultivation, and growing bacteria or fungi (microbes) to detect the presence or absence of microbes has conventionally been performed. In particular, since most of cell preparations for regenerative medicine are administered to a patient at the latest within two days after production, it is desired to expedite an examination that takes up to 14 days in the conventional method so that the presence or absence of microbes can be determined before administration.

As a method for detecting the growth of microbes, turbidity measurement is simple and generally used. However, it is difficult to detect the growth of microbes in a case of a specimen that is originally turbid, such as blood or a cell culture solution. As a method for detecting the growth of microbes other than turbidity measurement, PTL 1 discloses a method using an automatic measurement device that simultaneously detects the production and consumption of gas associated with the growth of microbes in multiple specimens. This automatic measurement device adopts fluorimetry in which a fluorescent dye whose fluorescence changes with a change in gas concentration of carbon dioxide, oxygen, or the like is fixed to a bottom of culture bottle, and a change in gas concentration due to microbial growth is detected by fluorescence. In the fluorescence method, it is known that a specimen is judged as positive when viable microbes grow up to $10^7$ CFU/mL (CFU: Colony forming unit) or more (NPL 1).

Further, as a method for detecting microbes with high sensitivity, a detection method by an ATP method (Adenosine Triphosphate) is known. The ATP method is a method for detecting ATP of a cell by bioluminescence by a luciferin-luciferase reaction, can generally detect microbes of about 100 CFU, and is highly sensitive. For example, PTL 2 discloses that a bacterial culture solution and a luminescent reagent are dispensed into a plate, and luminescence measurement by the ATP method is performed, so that growth and killing of bacteria are detected. Further, PTL 2 also discloses that a container is sealed and a gas supply mechanism is provided in order to enable detection of anaerobic bacteria.

CITATION LIST

Patent Literature

PTL 1: Japanese Patent No. 2696081
PTL 2: WO 2016/147313 A

Non-Patent Literature

NPL 1: Journal of Microbiology, Immunology and Infection (2015) 48, 419-424

SUMMARY OF INVENTION

Technical Problem

However, the fluorescence method described in PTL 1 has low sensitivity, and microbes cannot be detected unless viable microbes grow to $10^7$ CFU/mL or more. Therefore, in a case of a specimen with a small initial number of microbes or microbes with slow growth, it takes time to detect the microbes.

Further, in the conventional ATP method, there is a possibility that microbes are contaminated from the outside and a culture solution is contaminated by operation of fractionating the culture solution at each time period and mixing the fractionated culture solution with a luminescence reagent, which leads to false positive of the examination. If a luminescent reagent is mixed in advance with a culture solution and sealed, luminescence measurement can be continuously performed without fractionation operation. However, in the luciferin-luciferase reaction, since ATP and luciferin irreversibly react with each other and ATP is removed from a reaction system, ATP generated by microbes is always consumed in a luminescence reaction, the luminescence intensity decreases, and the sensitivity decreases. Furthermore, in a case where a luminescent reagent in which an ATP extraction reagent is mixed in advance is used for convenience of operation, the luminescent reagent that is an enzyme is inhibited by the ATP extraction reagent. For this reason, the luminescence intensity decreases and the sensitivity decreases.

In view of the above, the present disclosure provides a cell detection device and a cell detection method that make detection of a cell in a specimen by an ATP method highly sensitive and shorten a detection time.

Solution to Problem

The cell detection device according to the present disclosure is a cell detection device that detects a cell in a specimen. The cell detection device includes a sealed container having a sealable specimen introduction portion, a culture portion that holds a culture solution, an extraction reagent portion that holds an extraction reagent, and a luminescent reagent portion that holds a luminescent reagent, a contact mechanism that controls contact of the culture solution, the extraction reagent, and the luminescent reagent, a photodetector that detects luminescence from the luminescent reagent portion, and a calculator that calculates an amount of luminescence from a detection signal of the photodetector and determines growth of the cell based on a temporal change in the amount of luminescence. The extraction reagent is a reagent for extracting a substance necessary for a luminescence reaction with the luminescent reagent from the cell to obtain an extraction solution. The luminescent reagent is a reagent that emits light when brought into contact with the extraction solution. The culture solution, the extraction reagent, and the luminescent reagent are disposed separately in the sealed container, and the contact mechanism intermittently brings the culture solution to which the specimen is added and the extraction reagent into contact with each other to obtain the extraction solution, and intermittently brings the extraction solution and the luminescent reagent into contact with each other.

Further features related to the present disclosure will be clear from the description of the present description and the accompanying drawings. Further, the aspects of the present disclosure are achieved and realized by an element, a combination of various elements, detailed description below, and aspects of the claims.

The description of the present description is merely exemplary, and does not limit the scope of claims or application examples of the present disclosure in any sense.

Advantageous Effects of Invention

According to the present disclosure, detection of microbes in a specimen by the ATP method can be made highly sensitive, and detection time can be shortened.

An object, a configuration, and an advantageous effect other than those described above will be clarified in description of embodiments described below.

DESCRIPTION OF EMBODIMENTS

First Embodiment

<Configuration of Cell Detection Device>

Figures 1A, 1B, 1C:
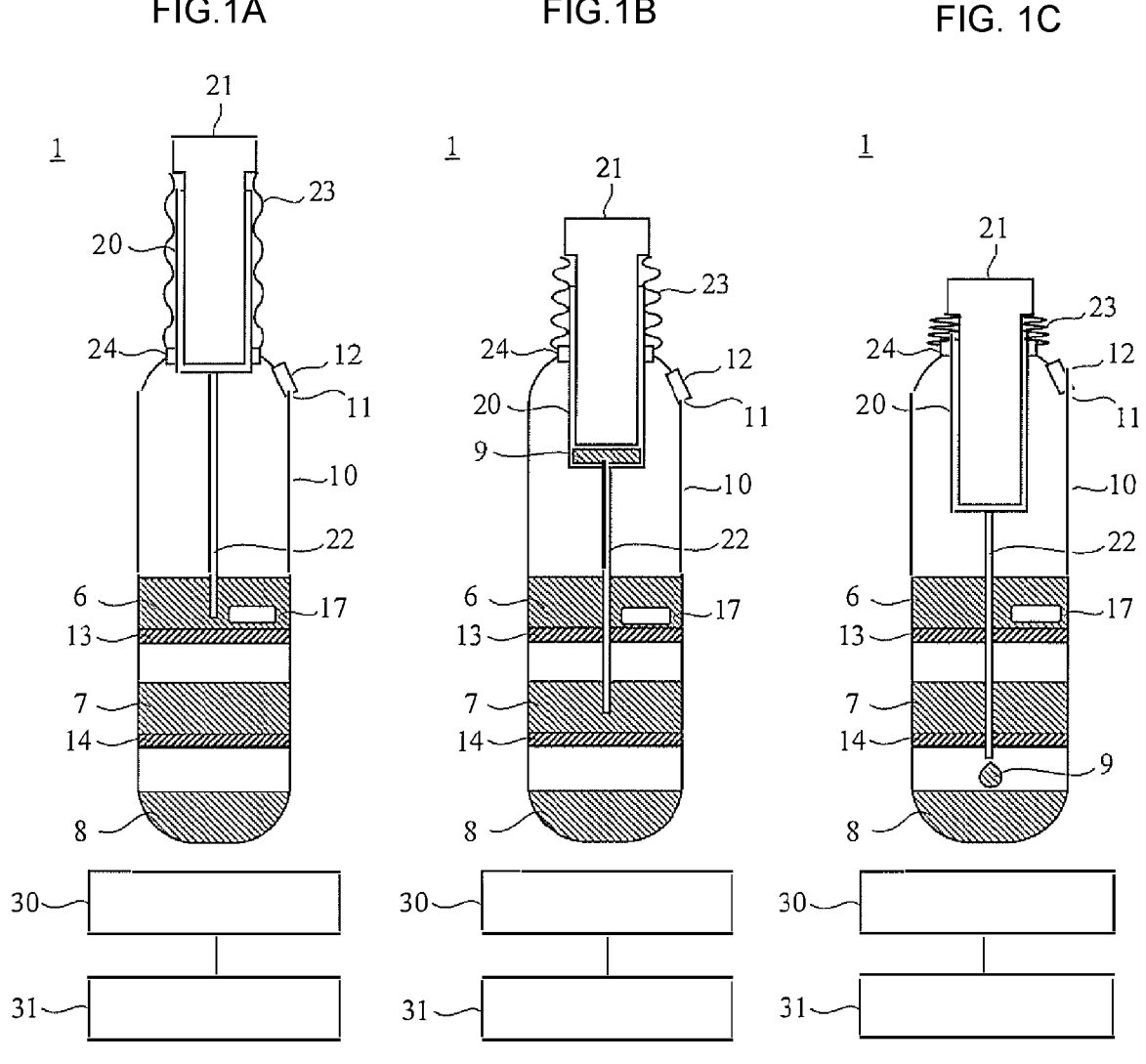
FIGS. 1A-1C are schematic views illustrating a configuration of a cell detection device according to a first embodiment.

FIGS. 1A-1C are schematic diagrams illustrating a configuration of a cell detection device 1 according to a first embodiment. As illustrated in FIG. 1A, the cell detection device 1 includes a sealed container 10, a syringe 20 (contact mechanism), a photodetector 30, and a calculation device 31 (calculator).

The sealed container 10 includes an opening portion 11 and a septum 12, and a septum 13 and a septum 14. The inside of the sealed container 10 is separated into three spaces by the septum 13 (first septum) and the septum 14 (second septum). A culture medium is introduced into a space (culture portion) above the septum 13. An ATP extraction reagent 7 is introduced into a space (extraction reagent portion) above the septum 14. A luminescent reagent 8 is introduced into a space (luminescent reagent portion) below the septum 14. In this manner, the culture portion is disposed above the extraction reagent portion, and the extraction reagent portion is disposed above the luminescent reagent portion, and a culture solution 6, the ATP extraction reagent 7, and the luminescent reagent 8 are held at positions separated from each other in the sealed container 10.

Note that, in the present description, "sealing" means that microorganisms do not pass through, and a pore and a gap having a size that microorganisms do not pass through, for example, a pore and a gap of 0.1 μm or less are acceptable. Therefore, a part of a wall of the sealed container 10 may be made from a material through which a cell is not allowed to pass and gas can pass. Examples of the material through which gas can pass include a membrane filter having a pore diameter of about 0.1 μm.

As described above, gas inside and outside the sealed container 10 is allowed to pass, so that a gas composition in the sealed container 10 can be controlled from the outside of the sealed container 10, and a gas composition suitable for the growth of microbes can be obtained. For example, in a case where luminescence measurement of anaerobic microbes is performed, oxygen-free gas is introduced into a space holding the culture solution 6 to set an anaerobic condition, and oxygen-containing gas can be introduced into a space holding the luminescent reagent 8. Alternatively, the sealed container 10 can be made from a material through which gas does not permeate, oxygen-containing gas can be introduced when the luminescent reagent 8 is enclosed, and oxygen-free gas can be introduced when a culture medium is enclosed, so that anaerobic culture is possible.

The opening portion 11 and the septum 12 (specimen introduction portion) fitted to the opening portion 11 are provided at a position (for example, an upper portion of the sealed container 10) through which a specimen can be introduced into the space (culture portion) above the septum 13. The specimen is a pharmaceutical product, a food product, a cosmetic product, a cell culture solution, a cell preparation, or the like for which the presence or absence of microbes is detected. The specimen is collected, for example, by the user with a specimen syringe (not illustrated), and is introduced into the culture medium above the septum 13 with a needle of the specimen syringe penetrating the septum 12. The specimen and the culture medium are mixed in this way, so that the culture solution 6 is obtained. A hole formed by piercing the needle of the specimen syringe is closed by an elastic force of the septum 12, and the sealed container 10 is sealed. This makes it possible to prevent mixing (contamination) of microorganisms from the outside at the time of specimen introduction.

The inside of the sealed container 10 may be sterilized, and the introduction of the specimen into the culture portion may be performed aseptically. Instead of the septum 12, another mechanism such as an openable and closable lid (for example, a fit-in lid or a screw cap) may be provided in the opening portion 11.

The culture medium may be a liquid culture medium or a lyophilized powder culture medium. When the culture medium is powdery, a solvent (such as a buffer solution) for forming a liquid culture medium is further introduced onto the septum 13. A component that promotes cell growth and a component that captures a substance that inhibits cell growth may be added to the culture medium in advance.

As described above, a specimen is added to the culture medium from the septum 12 fitted to the opening portion 11. Instead of providing the opening portion 11 and the septum 12, the configuration may be such that a specimen is collected with the syringe 20, and added to the culture medium on the septum 13 with the syringe 20 fitted to the sealed container 10.

The ATP extraction reagent 7 is a reagent for extracting ATP from the inside of a cell, and may include one capable of inactivating an ATP degrading enzyme. Specifically, when a substance in a microbial cell such as ATP is to be measured, for example, an aqueous solution containing a surfactant such as benzalkonium chloride or benzethonium chloride acting on a microbial membrane, trichloroacetic acid (TCA), a Tris buffer, ethanol, a lytic enzyme having protease activity, lysozyme, or the like can be used as the ATP extraction reagent 7. In a case where a substance produced by an enzyme of microbes is to be measured, an aqueous solution containing a substrate of the enzyme can be used instead of the ATP extraction reagent 7.

The luminescent reagent 8 is a reagent that emits light by being mixed with ATP. For example, a reagent containing luciferase and luciferin that emit light by a luciferin-luciferase reaction in the presence of ATP can be used. Note that luciferase may be introduced into the luminescent reagent 8, and luciferin may be mixed with the ATP extraction reagent 7. In a case where a substance produced by an enzyme of microbes is to be measured, a reagent that reacts with a substance produced by an enzyme of microbes to emit light can be used.

The syringe 20 (contact mechanism) is coupled to the upper portion of the sealed container 10. Packing 24 is provided between the syringe 20 and the sealed container 10 to maintain airtightness inside the sealed container 10. The syringe 20 includes a plunger 21, a syringe needle 22, and a cover 23. The syringe 20 is movable up and down, and the syringe needle 22 also moves up and down in conjunction with the syringe 20. The syringe 20 is provided to the user in a state where the tip of the syringe needle 22 is located in the space (culture portion) above the septum 13.

The syringe needle 22 has a length equal to or more than a distance by which the syringe 20 moves up and down in a series of operations for performing luminescence measurement. Specifically, the length of the syringe needle 22 is a length that allows the syringe needle 22 to penetrate the septa 13 and 14 when the syringe 20 is moved downward. By moving the plunger 21 up and down with respect to the syringe 20, the culture solution 6 and the ATP extraction reagent 7 can be sucked into or discharged from the syringe needle 22. The specimen may be any of solid, liquid, and gas as long as vertical movement of the syringe needle 22 and suction of the culture solution 6 are not hindered.

The septa 13 and 14 are formed of a material having an action of closing a through hole formed by the syringe needle 22 with an elastic force, such as silicone rubber. In this manner, even when the tip of the syringe needle 22 repeatedly penetrates the septa 13 and 14 a plurality of times, the culture solution 6 and the ATP extraction reagent 7 do not leak from the through-hole, and remain on the septa 13 and 14, respectively, so that the separated state can be maintained.

The syringe 20 is provided with the cover 23 that covers a side surface above the packing 24. The cover 23 has flexibility. The cover 23 is formed in, for example, a bellows shape, and expands and contracts in conjunction with vertical movement of the syringe 20. The cover 23 can prevent microorganisms attached to the outside of the syringe 20 from being contaminated in the culture solution 6 when the syringe 20 descends and enters the sealed container 10.

At least the vicinity of the luminescent reagent 8 in the sealed container 10 is formed of a material that transmits the wavelength of light emitted in the luminescent reaction. For example, in a case where the luminescent reagent 8 causes a reaction to emit visible light, colorless and transparent plastic, glass, or the like can be used as the material of the sealed container 10.

The photodetector 30 is disposed outside the sealed container 10 at a position where light emitted from the luminescent reagent 8 can be detected. The photodetector 30 detects light emitted from the luminescent reagent 8 at certain time intervals or constantly during culture, and outputs a detection signal to the calculation device 31. As the photodetector 30, for example, a photomultiplier tube, a CCD camera, a photodiode, or the like can be used.

The calculation device 31 performs calculation processing such as calculation of an amount of luminescence and determination of positive or negative on the basis of a detection signal received from the photodetector 30. Although not illustrated, the calculation device 31 may include a storage, a display and a speaker. The storage stores past measurement data and data such as a certain threshold for determining whether a specimen is positive or negative from an amount of luminescence derived from microbes. The display displays a calculated amount of luminescence and a determination result. The speaker emits an alarm sound indicating a determination result, and the like.

The calculation device 31 can calculate, as an amount of luminescence derived from microbes, a value (increase amount of an amount of luminescence) obtained by subtracting an amount of luminescence immediately before an ATP solution 9 (extraction solution) obtained by mixing the culture solution 6 and the ATP extraction reagent 7 is added to the luminescent reagent 8 from a maximum value of the amount of luminescence at the time of the addition. Further, the calculation device 31 can determine whether the specimen is positive (microbes are present in the specimen) or negative (microbes are not present in the specimen) by comparing a certain threshold set in advance with an amount of luminescence derived from microbes.

<Cell Detection Method>

Next, an example of the cell detection method using the cell detection device 1 according to the present embodiment will be described. The present method is a method in which the user manually performs luminescence measurement using the cell detection device 1.

First, the user collects a specimen using the specimen syringe, and introduces the specimen into the culture medium on the septum 13 by inserting a needle of the specimen syringe into the septum 12 to obtain the culture solution 6 (FIG. 1A).

An ATP eliminating reagent such as an ATP degrading enzyme may be added to the culture medium on the septum 13 in advance. In this manner, ATP contained in the culture medium and free ATP contained in the specimen can be decomposed. It is possible to measure only ATP in a microbial cell by eliminating ATP other than that in the microbial cell, and the detection sensitivity for ATP derived from microbes is improved.

If necessary, the culture solution 6 may be stirred by a method such as putting the tip of the syringe needle 22 of the syringe 20 into the culture solution 6 and moving up and down the plunger 21, swinging the sealed container 10 from the outside by a stirrer or manually, or putting a stirrer 17 (stirrer) into the culture medium. By stirring the culture solution 6, the growth of aerobic microbes can be promoted, and the time until detection of microbes can be shortened. Further, when a part of the culture solution 6 is sucked into the syringe 20, the culture solution 6 is uniform, and data with little variation can be obtained.

Next, in order to measure an amount of luminescence (initial concentration of microbes) at time zero, the user immerses the tip of the syringe needle 22 in the culture solution 6 and raises the plunger 21 to suck a certain amount of a part of the culture solution 6 into the syringe 20. Next, the user lowers the syringe 20 to allow the syringe needle 22 to penetrate the septum 13, immerses the tip of the syringe needle 22 in the ATP extraction reagent 7, and further raises the plunger 21 to suck a certain amount of a part of the ATP extraction reagent 7 into the syringe 20. A part of the previously sucked culture solution 6 and a part of the ATP extraction reagent 7 are mixed in the syringe 20, the microbes are broken, ATP in the microbes is taken out, and the ATP solution 9 is obtained (FIG. 1B).

Next, the user lowers the syringe 20 further to allow the syringe needle 22 to penetrate the septum 14, and then lowers the plunger 21 to add the ATP solution 9 in the syringe 20 to the luminescent reagent 8 (FIG. 1C). At this time, the photodetector 30 detects luminescence due to contact between the ATP solution 9 and the luminescent reagent 8, and outputs a detection signal to the calculation device 31. The calculation device 31 receives the detection signal of the photodetector 30, and calculates, as the amount of luminescence at time zero, a value (increase amount of the amount of luminescence) obtained by subtracting the amount of luminescence immediately before dropping of the ATP solution 9 from the maximum value of the amount of luminescence after the dropping.

After culture for a certain time, for example, after one hour later, the user operates the syringe 20 to immerse the tip of the syringe needle 22 in the culture solution 6. Then, the suction of the culture solution 6, the suction of the ATP extraction reagent 7, the addition of the ATP solution 9 to the luminescent reagent 8, and the luminescence measurement are performed again in the same procedure as described above. Note that the culture of the culture solution 6 may be performed while the temperature is adjusted in a culture vessel (temperature adjuster) (not illustrated).

By the above operation, the measurement of the amount of luminescence is repeated every certain time, and the growth of microbes is determined from the temporal change of the amount of luminescence. Note that the time interval (culture time) may be constant or may be changed at an appropriate timing.

The calculation device 31 regards the microbes as having grown and determines positive when the amount of luminescence of the entire culture solution 6 or the amount of luminescence derived from microbes is equal to or more than a preset threshold.

The threshold of the amount of luminescence for determining the specimen as positive can be set to, for example, a value obtained by tripling the amount of luminescence at time zero. Alternatively, the threshold can also be set to a value obtained by calculating the standard deviation of the amount of luminescence at time zero in a plurality of measurements and adding three times the standard deviation of the amount of luminescence at time zero to the amount of luminescence at time zero. In a case where it is desired to improve the reliability of the determination as positive, for example, the threshold can be set to a value obtained by multiplying the amount of luminescence at time zero by ten or a value obtained by adding a value obtained by multiplying the standard deviation of the amount of luminescence at time zero by ten to the amount of luminescence at time zero. Alternatively, for example, luminescence measurement may be performed a plurality of times under the same conditions (same initial microbial concentration, same temperature, and the like), an average value of the amounts of luminescence in the culture time during which positive is determined may be calculated, and the average value may be used as the threshold. Alternatively, a recommended threshold may be set for each type of microbes to be measured, or the threshold may be set by the user before measurement or during measurement.

Note that the present embodiment may have a configuration in which the ATP extraction reagent 7 is disposed on the septum 13, and the culture solution 6 is disposed on the septum 14.

The method of detecting ATP by a luciferin-luciferase reaction is described above. There is also a method of generating active oxygen by a quinone oxidoreductase (NA- DPH or NADH) of viable microbes in the presence of quinone, for example, and using a chemiluminescent reagent for quantifying the active oxygen. In this case, as the luminescent reagent 8, a chemiluminescent reagent is introduced into the lowermost portion of the sealed container 10 (space below the septum 14), and a quinone solution is introduced onto the septum 14. When the culture solution 6 and the quinone solution are sucked into the syringe 20 and mixed, active oxygen is generated by the reaction of the quinone and the quinone oxidoreductase, and when this solution is added dropwise to the chemiluminescent reagent, the chemiluminescent reagent reacts with the active oxygen to emit light. Since active oxygen increases in amount in accordance with the growth of microbes, the amount of luminescence proportional to the growth of microbes can be measured.

Examples of the chemiluminescent reagent include 2-methyl-6-phenyl-3, 7-dihydroimidazo[1,2-a]pyrazin-3-one (CLA), 2-methyl-6-(4-methoxyphenyl)-3, 7-dihydro-imidazo[1,2-a]pyrazin-3-one (MCLA), 2-methyl-6-p-methoxyphenylethynylimidazopyrazinone (MPEC), an indocyanine imidazopyrazinone compound (NIR-CLA), and the like.

In the present embodiment, the case where the culture portion, the extraction reagent portion, and the luminescent reagent portion are arranged in the vertical direction, and the syringe 20 moves up and down is described. The present invention is not limited to the above. The configuration may be such that the culture portion, the extraction reagent portion, and the luminescent reagent portion are arranged in, for example, the horizontal direction, and the syringe 20 moves in the horizontal direction.

<Technical Effect>

As described above, the present embodiment employs the configuration in which the culture solution 6, the ATP extraction reagent 7, and the luminescent reagent 8 are held in the sealed container 10 so as to be disposed at separated positions, a part of the culture solution 6 and a part of the ATP extraction reagent 7 are sucked into the syringe 20 to obtain the ATP solution 9, and the ATP solution 9 is added to the luminescent reagent 8. In this manner, since ATP of microbes is extracted and then mixed with the luminescent reagent 8, ATP of microbes can be detected with high sensitivity, and the growth of microbes can be detected in a short time. Further, since it is not necessary to perform operation of fractionating the culture solution 6 by a manual pipetter or the like and mixing the culture solution 6 with the luminescent reagent 8 for each culture time, it is possible to prevent false positives due to contamination of microorganisms from the outside.

Furthermore, since the culture solution 6, the ATP extraction reagent 7, and the luminescent reagent 8 are separated and are caused to contact with each other intermittently, ATP produced by microbes is not always consumed in a luminescent reaction. In this manner, since the ATP concentration in the culture solution 6 increases in proportion to the growth of microbes, the growth of microbes can be detected with high sensitivity. Further, as compared with the case of using a reagent in which the ATP extraction reagent 7 and the luminescent reagent 8 are mixed in advance, inhibition of the luminescent reagent 8 is suppressed, and ATP measurement with highly sensitive is possible. Therefore, the growth of microbes can be detected with high sensitivity, and luminescence measurement can be performed in a shorter time than in the conventional turbidity method or fluorescence method.

Second Embodiment

<Configuration of Cell Detection Device>

Figure 2:
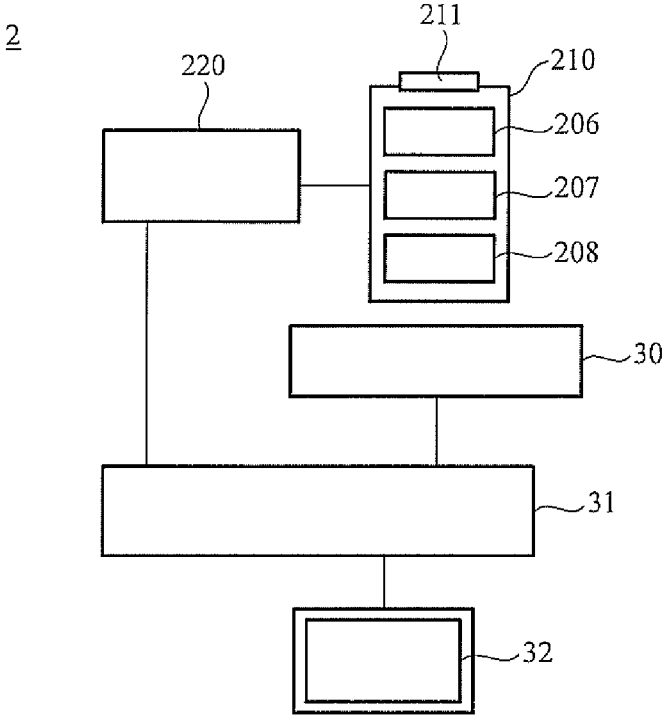
FIG. 2 is a schematic view illustrating a configuration of the cell detection device according to a second embodiment.

FIG. 2 is a schematic diagram illustrating a configuration of a cell detection device 2 according to a second embodiment. The cell detection device 2 of the present embodiment is different from that of the first embodiment in that the cell detection device 2 is a device that automatically performs luminescence measurement. Description of configurations similar to those of the first embodiment will be omitted.

As illustrated in FIG. 2, the cell detection device 2 includes a sealed container 210, a contact mechanism 220, the photodetector 30, the calculation device 31, and a display 32.

The sealed container 210 may have the same configuration as the sealed container 10 according to the first embodiment, for example. The sealed container 21 includes a specimen introduction portion 211, a culture portion 206, an extraction reagent portion 207, and a luminescent reagent portion 208. The culture portion 206 is disposed above the extraction reagent portion 207, and the extraction reagent portion 207 is disposed above the luminescent reagent portion 208.

A specimen is introduced from the specimen introduction portion 211 into the culture portion 206. The specimen introduction portion 211 has a structure capable of sealing the sealed container 210 after introduction of a culture solution into the culture portion 206, and prevents mixing (contamination) of microbes from the outside. For example, similarly to the first embodiment, the specimen introduction portion 211 may include an opening portion provided on the sealed container 210 and a septum fitted to the opening portion.

The culture portion 206 holds a culture solution containing a specimen and a culture medium. The extraction reagent portion 207 holds an ATP extraction reagent for extracting a substance to be measured from a cell. The luminescent reagent portion 208 holds a luminescent reagent that emits light when brought into contact with ATP. In the sealed container 210, the culture portion 206, the extraction reagent portion 207, and the luminescent reagent portion 208 are disposed separately from each other, so that the culture solution, the ATP extraction reagent, and the luminescent reagent are held at separate positions.

The contact mechanism 220 is a mechanism that controls contact of a culture solution of the culture portion 206, an ATP extraction reagent of the extraction reagent portion 207, and a luminescent reagent of the luminescent reagent portion 208. The contact mechanism 220 may be provided outside the sealed container 210 in order to prevent contamination of the culture solution. When the cell detection device 1 of the first embodiment being automated is assumed as the cell detection device 2 of the present embodiment, the contact mechanism 220 includes, for example, the syringe 20 and a syringe driving device that drives the syringe 20. In this case, the syringe driving device has actuators for driving each of the syringe 20 and the plunger 21. As the actuators, for example, a ball screw type actuator or the like can be used.

In the storage of the calculation device 31, data related to the position and thickness of the septa 13 and 14, data related to the amount of the culture medium or the culture solution 6, the amount of the ATP extraction reagent 7, the amount of the luminescent reagent 8, and the like may be stored in advance. The calculation device 31 may move the position of the syringe 20 and the plunger 21 to a certain origin position before operation of luminescence measurement is started, calculate a movement amount of the syringe 20 and the plunger 21 on the basis of the above data, a distance from the certain origin position, and the like, and control the syringe driving device. The certain origin position of the syringe 20 can be, for example, a position where the tip of the syringe needle 22 is immersed in the culture medium.

Although not illustrated, the cell detection device 2 may include a specimen syringe for introducing a specimen from the specimen introduction portion 211 and a specimen syringe driver for controlling driving of the specimen syringe. In this case, the specimen syringe driver drives the specimen syringe to collect a specimen, causes a needle of the specimen syringe to penetrate the specimen introduction portion 211, and adds the specimen to the culture portion 206.

The calculation device 31 is connected to the specimen syringe driver, the contact mechanism 220, the photodetector 30, and the display 32, and controls operation of these. The display 32 displays various pieces of data such as a measurement result, a GUI screen, and the like in accordance with an instruction from the calculation device 31.

<Cell Detection Method>

Figure 3:
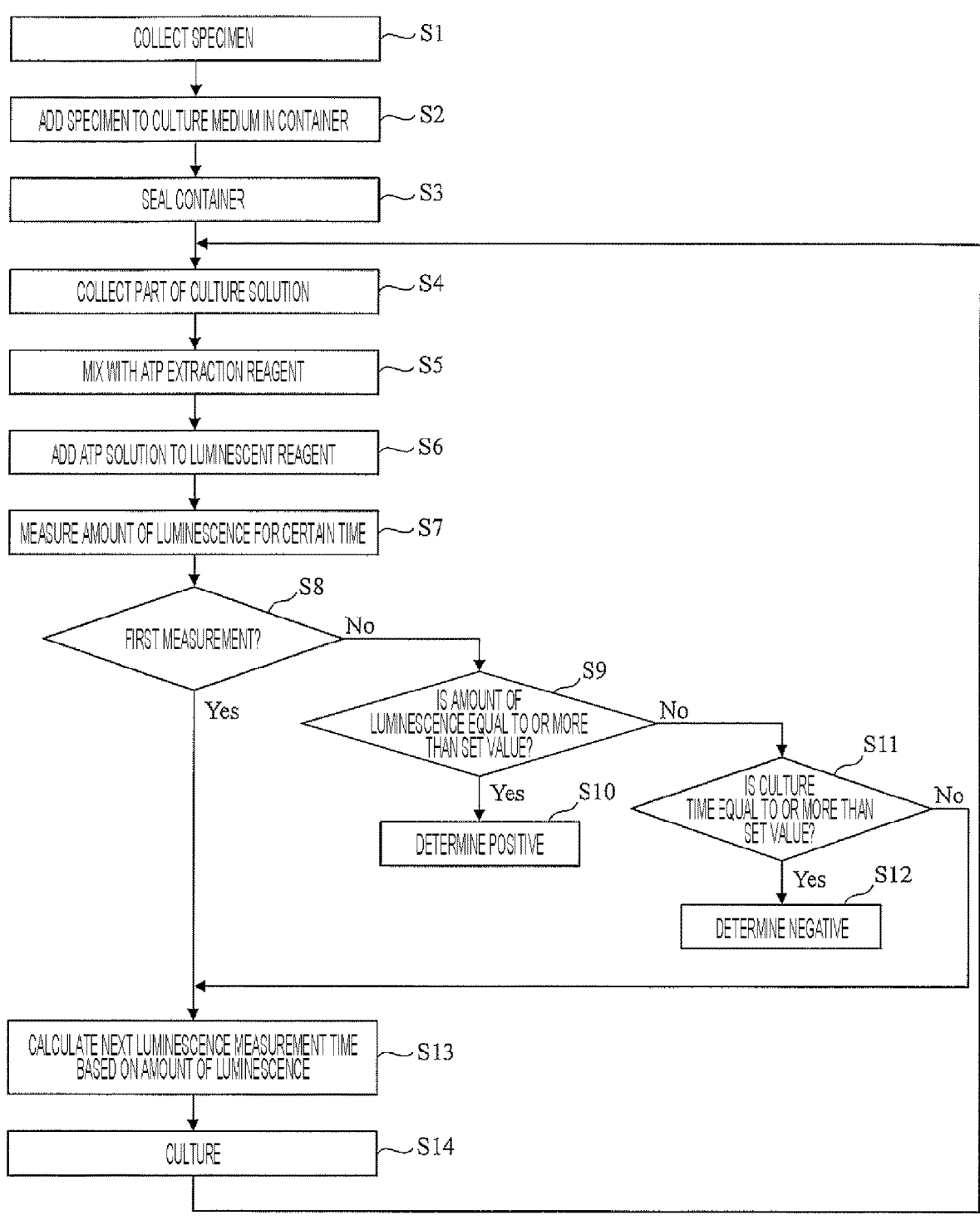
FIG. 3 is a flowchart illustrating an example of a cell detection method using the cell detection device according to the second embodiment.

FIG. 3 is a flowchart illustrating an example of the cell detection method using the cell detection device 2 according to the second embodiment. Hereinafter, an example in which the sealed container 10 of the first embodiment (FIGS. 1A-1C) is used as the sealed container 210 and the syringe 20 and the syringe driving device are used as the contact mechanism 220 will be described.

First, in Step S1, the calculation device 31 drives the specimen syringe driver to collect a specimen with a specimen syringe (not illustrated). At this time, the calculation device 31 may drive the syringe driving device to move the syringe 20 and the plunger 21 to a certain origin position. Next, in Step S2, the calculation device 31 drives the specimen syringe driver to cause the needle of the specimen syringe to penetrate the specimen introduction portion 211, and adds the specimen to the culture medium in the culture portion 206 to obtain the culture solution 6. In a case where the specimen introduction portion 211 is a septum, the sealed container 210 is sealed as the specimen syringe is pulled from the septum in Step S3.

Next, in Step S4, the calculation device 31 drives the syringe driving device to raise the plunger 21 by a certain amount to collect a part of the culture solution 6 into the syringe 20.

In Step S5, the calculation device 31 drives the syringe driving device to move the syringe 20 downward, and causes the syringe needle 22 to penetrate the septum 13. The calculation device 31 calculates, for example, a distance from the certain origin position to the ATP extraction reagent 7, so that driving of the syringe 20 is stopped after the syringe 20 is driven until the tip of the syringe needle 22 is immersed in the ATP extraction reagent 7. After the above, the calculation device 31 moves the plunger 21 upward by the syringe driving device, and sucks a certain amount of the ATP extraction reagent 7, so that the ATP extraction reagent 7 is mixed with the culture solution 6 collected in the syringe 20. In this manner, microbes in the culture solution 6 are destroyed, ATP is extracted, and the ATP solution 9 is obtained.

Next, in Step S6, the calculation device 31 moves the syringe 20 downward by the syringe driving device to cause the syringe needle 22 to penetrate the septum 14. After the above, the plunger 21 is moved downward by the syringe driving device, and the ATP solution 9 in the syringe 20 is discharged and mixed with the luminescent reagent 8. In this manner, the luminescent reagent 8 reacts with ATP, and luminescence is obtained.

In Step S7, the photodetector 30 measures the generated luminescence for a certain time determined in advance, and outputs the detected amount of luminescence to the calculation device 31.

In Step S8, the calculation device 31 determines whether or not the current measurement is the first measurement. In a case where the current measurement is the first measurement (Yes), the processing proceeds to Step S13.

In Step S13, the calculation device 31 calculates a next luminescence measurement time from the measured amount of luminescence. The next luminescence measurement time calculated in Step S13 may not be changed for each measurement, and may be set, for example, after one hour each time or the like. Alternatively, as the next luminescence measurement time, changes may be made for each measurement in such a manner that, for example, a first luminescence measurement is performed after one hour from the start of culture, a second luminescence measurement is performed after two hours from the first measurement, and the third luminescence measurement is performed after three hours from the second measurement.

After the above, in Step S14, the calculation device 31 stops driving of the syringe 20 and the plunger 21 until the next luminescence measurement time, and performs culture at a temperature suitable for microbial growth. When the next luminescence measurement time is reached, the calculation device 31 returns to Step S4 again, and executes Steps S4 to S8 in the same manner as described above.

In the second and subsequent measurements (No in Step S8), in Step S9, the calculation device 31 determines whether the amount of luminescence is equal to or more than a set value.

When the amount of luminescence is equal to or more than the set value (Yes), the processing proceeds to Step S10, and the calculation device 31 determines that the growth of microbes is detected and outputs determination of positive. At this time, the calculation device 31 may display the determination result on the display 32.

When the amount of luminescence is less than the set value (No), the processing proceeds to Step S11, and the calculation device 31 determines whether or not the culture time is equal to or more than the set value.

When the culture time is equal to or more than the set value (Yes), the processing proceeds to Step S12, and the calculation device 31 determines that microbial growth is not detected and outputs determination of negative.

When the culture time is less than the set value (No), the processing proceeds to Step S13, and the calculation device 31 calculates the next luminescence measurement time from the transition of the measured amount of luminescence. After the above, culture is further performed in Step S14. By repeating this after the above, luminescence measurement is performed.

Note that, in a case where a container in which the positions of the culture portion 206 and the extraction reagent portion 207 are reversed is used as the sealed container 210, the order of Steps S4 and S5 may be reversed, and the ATP extraction reagent may be sucked first.

<Technical Effect>

As described above, the second embodiment employs the configuration in which the operation of mixing a part of the culture solution and the ATP extraction reagent in the sealed container 210 to obtain the ATP solution and adding the ATP solution to the luminescent reagent is automatically performed. In this manner, it is possible to reduce the burden on operation by the user while achieving the same effects as those of the first embodiment.

In the conventional automated cell detection device, a mechanism for performing a complicated fractionating operation such as sucking and discharging a culture solution or making a pipette tip disposable is necessary, and there has been a problem that the device is complicated. In contrast, the present embodiment does not require a mechanism for performing a fractionating operation as in the above-described configuration, and a device can have a simple configuration.

Third Embodiment

<Configuration of Cell Detection Device>

Figure 4:
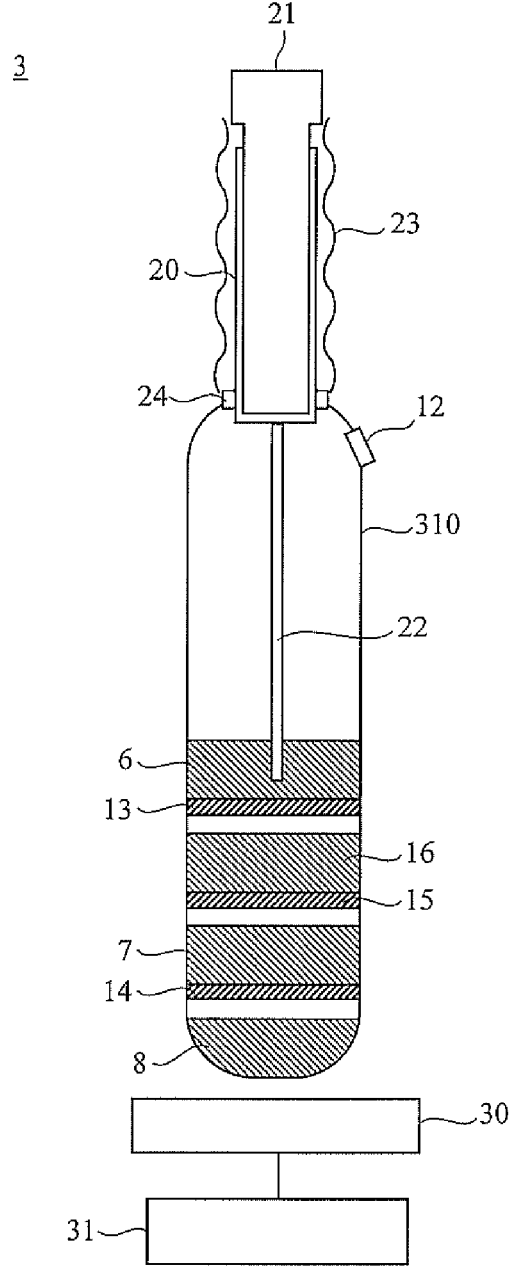
FIG. 4 is a schematic view illustrating a configuration of the cell detection device according to a third embodiment.

FIG. 4 is a schematic diagram illustrating a configuration of a cell detection device 3 according to a third embodiment. The cell detection device 3 of the present embodiment is different from that of the first embodiment in that a septum 15 is further included between the septa 13 and 14 inside a sealed container 310, and an ATP eliminating reagent 16 is introduced onto the septum 15. Description of configurations similar to those of the first embodiment will be omitted.

As illustrated in FIG. 4, the inside of the sealed container 310 is separated into four spaces by the septa 13 to 15. A culture medium is introduced into a space (culture portion) above the septum 13. The ATP eliminating reagent 16 is introduced into a space (eliminating reagent portion) above the septum 15. The ATP extraction reagent 7 is introduced into a space (extraction reagent portion) above the septum 14. The luminescent reagent 8 is introduced into a space (luminescent reagent portion) below the septum 14. In this manner, the culture portion, the eliminating reagent portion, the extraction reagent portion, and the luminescent reagent portion are arranged in this order from the top to the bottom, and the culture solution 6, the ATP eliminating reagent 16, the ATP extraction reagent 7, and the luminescent reagent 8 are located at separated places in the sealed container 310.

The ATP eliminating reagent 16 is a reagent that eliminates free ATP outside a microbial cell. After the ATP eliminating reagent 16 eliminates free ATP in the culture solution 6, ATP inside a microbial cell is extracted by the ATP extraction reagent 7, so that only ATP of viable microbes can be measured.

Note that the present embodiment may have a configuration in which the ATP eliminating reagent 16 is disposed on the septum 13, and the culture solution 6 is disposed on the septum 15.

<Cell Detection Method>

Next, an example of the cell detection method using the cell detection device 3 according to the present embodiment will be described. The present method is a method in which the user manually performs luminescence measurement using the cell detection device 3.

In the cell detection method of the present embodiment, after or before a part of the culture solution 6 is sucked with the syringe 20, a part of the ATP eliminating reagent 16 is sucked with the syringe 20 and mixed with the culture solution 6. After the above, the mixture is allowed to stand for a certain period of time so that ATP outside a microbial cell in the culture solution 6 is eliminated. The other points are similar to those of the first embodiment, and are omitted from the description.

<Technical Effect>

As described above, the present embodiment has a step of eliminating ATP outside a microbial cell in the culture solution 6 by the ATP eliminating reagent 16 separated from the culture solution 6, the ATP extraction reagent 7, and the luminescent reagent 8. In this manner, the background of luminescence measurement can be lowered, and ATP of microbes can be detected with high sensitivity, so that growth of microbes can be detected in a short time.

Fourth Embodiment

<Configuration of Cell Detection Device>

Figure 5:
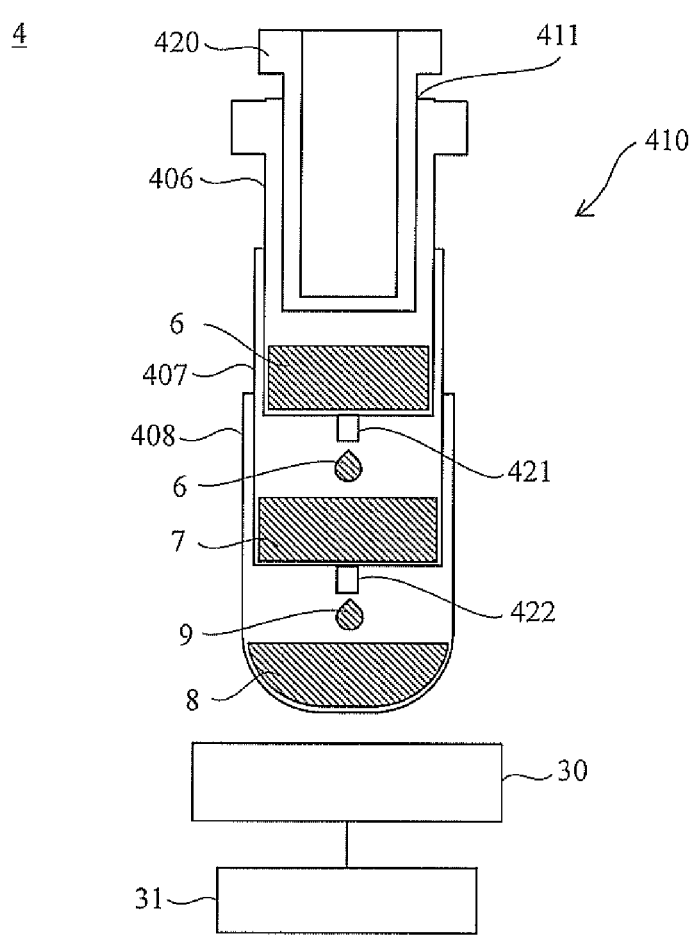
FIG. 5 is a schematic view illustrating a configuration of the cell detection device according to a fourth embodiment.

FIG. 5 is a schematic diagram illustrating a configuration of a cell detection device 4 according to a fourth embodiment. The cell detection device 4 of the present embodiment is different from that of the first embodiment in that a sealed container 410 includes a syringe 406 (culture portion), a container 407 (extraction reagent portion), and a container 408 (luminescent reagent portion).

The syringe 406 (first container) is fitted into the container 407 (second container) and is movable up and down with respect to the container 407. A plunger 420 movable up and down in the syringe 406 is fitted to the syringe 406. The syringe 406 is provided with a flow path 421 for dropping the culture solution 6 into the container 407.

The container 407 is fitted into the container 408 (third container), and is fixed at a position where a space is formed inside the container 408. The container 407 is provided with a flow path 422 for dropping the ATP solution into the container 408.

A culture medium is held in the syringe 406. The ATP extraction reagent 7 is held in the container 407. The luminescent reagent 8 is held in the container 408. A specimen is added to the culture medium in the syringe 406 from an opening portion 411 (specimen introduction portion) by removal of the plunger 420, so that the culture solution 6 is obtained. As described above, the culture solution 6, the ATP extraction reagent 7, and the luminescent reagent 8 are located in separated places in the sealed container 410.

The flow paths 421 and 422 are set to have a material and a hole diameter that allow the solution to pass only in a case where a certain pressure or more is applied to the syringe 406 and the container 407. In this manner, the culture solution 6, the ATP extraction reagent 7, and the luminescent reagent 8 can be kept in a separated state in the sealed container 410.

<Cell Detection Method>

Next, an example of the cell detection method using the cell detection device 4 according to the present embodiment will be described. The present method is a method in which the user manually performs luminescence measurement using the cell detection device 4.

First, the user removes the plunger 420 from the syringe 406, and adds a specimen collected with the specimen syringe to the culture medium to obtain the culture solution 6. By fitting the plunger 420 to the syringe 406 again, the syringe 406 is sealed.

Next, the user lowers the plunger 420 to drop a certain amount of a part of the culture solution 6 from the flow path 421 and mixes the dropped solution with the ATP extraction reagent 7. In this manner, microbes in the culture solution 6 are destroyed, and ATP is extracted.

Next, the user lowers the syringe 406 to drop a certain amount of the ATP extraction reagent 7 (ATP solution 9) containing the extracted ATP from the flow path 422 to the luminescent reagent 8. In this manner, luminescence according to the amount of ATP in the ATP solution 9 is obtained.

The user repeatedly performs the above operation at certain time intervals, and measures a temporal change of the amount of luminescence. The other points of the cell detection method of the present embodiment, which are same as those of the first embodiment, will be omitted from description.

<Technical Effect>

In the first embodiment, the culture solution 6, the ATP extraction reagent 7, and the luminescent reagent 8 are sucked and discharged with the syringe 20, and the syringe needle 22 is caused to penetrate the septa 13 and 14 to mix them. However, as the penetration of the syringe needle 22 is repeated, there is a possibility that the through hole of the septa 13 and 14 is widened, liquid leaks, and an unintended reaction occurs. In contrast, in the present embodiment, mixing of the culture solution 6, the ATP extraction reagent 7, and the luminescent reagent 8 only requires dropping of the culture solution 6 from the flow path 421 and dropping of the ATP solution 9 from the flow path 422. Accordingly, it is possible to prevent an unintended reaction due to leakage of the culture solution 6, the ATP extraction reagent 7, and the luminescent reagent 8. Therefore, the reliability of the luminescence measurement can be further improved.

Fifth Embodiment

<Configuration of Cell Detection Device>

Figure 6:
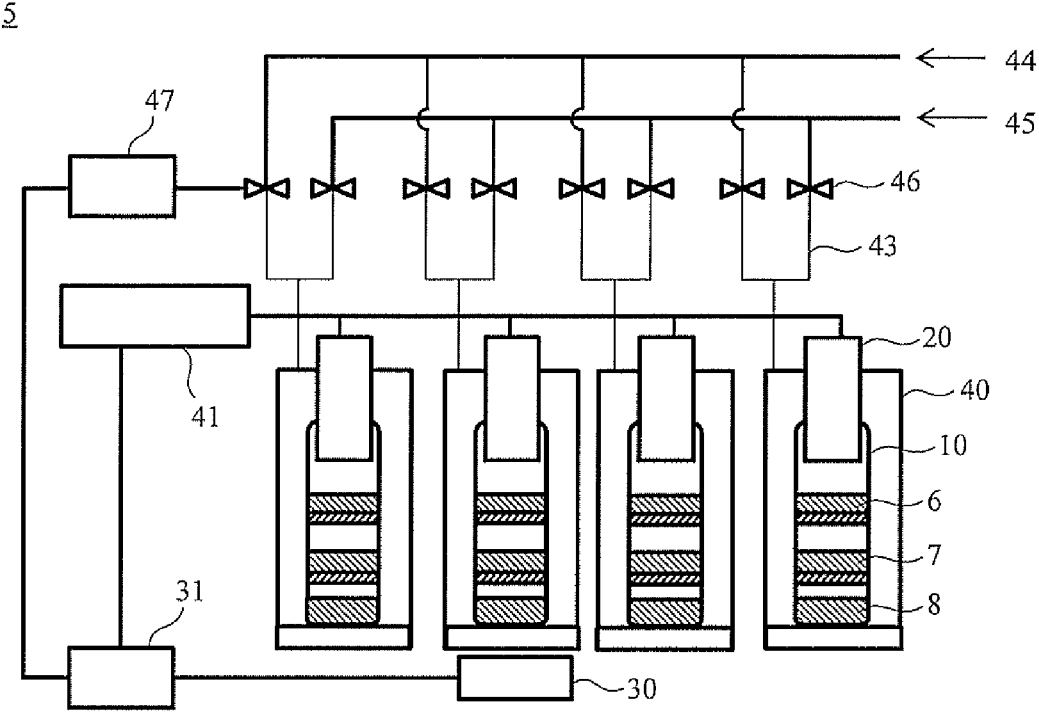
FIG. 6 is a schematic view illustrating a configuration of the cell detection device according to a fifth embodiment.

FIG. 6 is a schematic diagram illustrating a configuration of a cell detection device 5 according to a fifth embodiment. As illustrated in FIG. 6, the cell detection device 5 is a device that simultaneously and automatically measures luminescence of a plurality of the sealed containers 10. In FIG. 6, four of the sealed containers 10 are disposed. However, the number is not limited.

The cell detection device 5 includes a plurality of the sealed containers 10, a plurality of the syringes 20 fitted to the sealed containers 10 and a syringe driving device 41 (contact mechanism), a plurality of chambers 40 (temperature adjuster) covering the sealed containers 10, gas supply pipes 43, valves 46 and a valve driving device 47, and the calculation device 31. Since the sealed container 10 and the syringe 20 similar to those of the first embodiment (FIGS. 1A-1C) are used, the description of each configuration is omitted. Note that, as the sealed container, one in the third embodiment (FIG. 4) or the fourth embodiment (FIG. 5) can also be employed.

The calculation device 31 controls the photodetector 30, the syringe driving device 41, and the valve driving device 47.

The chambers 40 adjust the temperature of the sealed containers 10. In this manner, microbes can be cultured at a temperature suitable for each specimen, and growth can be performed under an optimal condition.

The syringe driving device 41 controls driving of the syringe 20 and the plunger 21 according to an instruction from the calculation device 31. The syringe driving device 41 includes actuators for driving the syringe 20 and the plunger 21. As the actuators, for example, a ball screw type actuator or the like can be used.

The gas supply pipes 43 are pipes for introducing gas 44 or gas 45 into each of the chambers 40. The gas 45 is, for example, gas containing oxygen. The gas 44 is, for example, gas containing no oxygen. The gas supply pipes 43 may be provided with a filter for preventing contamination, and the gas 44 or 45 may be supplied to the chamber 40 through the filter.

The valves 46 change passing and non-passing of the gas 44 or 45 to the gas supply pipes 43 by opening and closing of the valves 46. The valve driving device 47 controls opening and closing of each of the valves 46 according to an instruction from the calculation device 31. Although not illustrated, the valve driving device 47 is connected to each of the valves 46 to control opening and closing of the valves.

As the introduction of the gas 44 and the gas 45 into the chamber 40 is controlled by the valve 46, the gas concentration can be managed for each of the chambers 40. A part of the sealed container 10 can be made from a material (for example, a membrane filter or the like) that does not transmit microbes but transmits gas. In this manner, anaerobic microbes or aerobic microbes can be cultured for each of the sealed containers 10, and both anaerobic microbes and aerobic microbes can be simultaneously detected. Alternatively, in a case where a detection target is an animal cell, pH of a culture medium can be maintained at an appropriate value by adjustment of the concentration of carbon dioxide.

An identification number such as a barcode may be assigned to each of the sealed containers 10. Information such as an identification number of each of the sealed containers 10 and the type of a specimen may be stored in advance in the storage of the calculation device 31. The calculation device 31 may perform luminescence measurement at the same or different time intervals on the basis of the information stored in the storage, and acquire a temporal change in the amount of luminescence for a plurality of the sealed containers 10 in parallel.

The time required for conversion to positivity varies depending on an initial concentration and a type of microbes. In order to prevent microbes from being contaminated from the outside, it is necessary not to take in and out a specimen from the outside after the sealed container 10 is sealed. Accordingly, the number of times of luminescence measurement is limited by the culture solution amount at the initial measurement. In view of the above, when the amount of luminescence is measured at certain time intervals, the calculation device 31 can be programmed to automatically widen the time interval of the luminescence measurement in a case where it is determined that the change in the amount of luminescence from the previous measurement is small and the growth is slow. This makes it possible to measure a long-term temporal change according to microbes that grow slowly.

The cell detection device 5 may include a transport mechanism that moves one or both of the sealed container 10 and the photodetector 30 to a position where luminescence measurement can be performed. Note that a plurality of the photodetectors 30 may be prepared and provided for each of the sealed containers 10. In this manner, a transport mechanism for moving the sealed container 10 or the photodetector 30 is unnecessary, and the size of the cell detection device 5 can be reduced. Alternatively, as illustrated in FIG. 6, the number of the photodetectors 30 may be one, and by transporting the sealed container 10 to a position where the photodetector 30 can detect luminescence or by moving the photodetector 30 to the sealed container 10, it is not necessary to install a plurality of the photodetectors 30, and the cost can be reduced.

<Cell Detection Method>

The cell detection method using the cell detection device 5 of the present embodiment, for which, for example, the same method as the cell detection method of the second embodiment (FIG. 3) can be employed, will be omitted from description.

<Technical Effect>

As described above, the present embodiment employs the configuration in which a plurality of the sealed containers 10 are included and the luminescence measurement is performed simultaneously for a plurality of specimens. Accordingly, the measurement time can be shortened. Furthermore, the present embodiment employs the configuration capable of supplying gas having different compositions to each of a plurality of sealed containers 10. Accordingly, it is possible to simultaneously perform luminescence measurement of different microbial species such as anaerobic bacteria and aerobic bacteria.

[Variation]

The present disclosure is not limited to the above-described embodiments, and includes various variations. For example, the above embodiments are described in detail for easy understanding of the present disclosure, and it is not necessary to include all the described configurations. Further, a part of one embodiment can be replaced with a configuration of another embodiment. Further, a configuration of one embodiment can be added to a configuration of another embodiment. Further, for a part of configuration of the embodiments, a part of a configuration of another embodiment can be added, deleted, or substituted.

REFERENCE SIGNS LIST

1 to 5 cell detection device
6 culture solution
7 ATP extraction reagent
8 luminescent reagent
9 ATP solution
10, 210, 310, 410 sealed container
11 opening portion
12 to 15 septum
16 ATP eliminating reagent
17 stirrer
20 syringe
21 plunger
22 syringe needle
23 cover
2 packing
30 photodetector
31 calculation device
32 display
206 culture portion
207 extraction reagent portion
208 luminescent reagent portion
211 specimen introduction portion
220 contact mechanism
406 syringe
407 container
408 container
411 opening portion
420 plunger
421, 422 flow path
40 chamber
41 syringe driving device
43 gas supply pipe
44, 45 gas
46 valve
47 valve driving device

The invention claimed is:

1. A cell detection device that detects a cell in a specimen, comprising:

a sealed container having a sealable specimen introduction portion, a culture portion that holds a culture solution, an extraction reagent portion that holds an extraction reagent, and a luminescent reagent portion that holds a luminescent reagent;

a contact mechanism that controls contact of the culture solution, the extraction reagent, and the luminescent reagent;

a photodetector disposed outside the sealed container at a position that detects luminescence light emitted from the luminescent reagent in the luminescent reagent portion; and a processor configured to calculate an amount of luminescence from a detection signal received from the photodetector and determine growth of the cell based on a temporal change in the amount of luminescence, wherein the extraction reagent is a reagent for extracting a substance necessary for a luminescence reaction with the luminescent reagent from the cell to obtain an extraction solution, the luminescent reagent is a reagent that emits light when brought into contact with the extraction solution, the culture solution, the extraction reagent, and the luminescent reagent are disposed separately in the sealed container, the contact mechanism is disposed at an end of the sealed container and is movable airtightly in a direction of an interior of the sealed container, and is constructed to have a plurality of positions along the direction of the interior of the sealed container comprising a first position which brings a part of the culture solution to which the specimen is added and the extraction reagent into contact with each other to obtain the extraction solution, and a second position which brings the extraction solution and the luminescent reagent into contact with each other, and the extraction reagent portion is disposed between the culture portion and the luminescent reagent portion.

2. The cell detection device according to claim 1, wherein the luminescent reagent portion includes luciferase as the luminescent reagent, one or both of the luminescent reagent portion and the extraction reagent portion have luciferin, the extraction reagent is a reagent for extracting ATP from the cell, and the photodetector detects luminescence generated when the luciferase catalyzes a reaction between the ATP extracted from the cell and the luciferin.

3. The cell detection device according to claim 2, wherein the culture portion further includes an ATP eliminating reagent.

4. The cell detection device according to claim 2, wherein the sealed container further includes an eliminating reagent portion that holds an ATP eliminating reagent, and the eliminating reagent portion is disposed separately from the culture portion, the extraction reagent portion, and the luminescent reagent portion in the sealed container.

5. The cell detection device according to claim 1, further comprising:

a plurality of the sealed containers.

6. The cell detection device according to claim 1, further comprising:

a driving device that controls driving of the contact mechanism, wherein the driving device controls contact between the culture solution and the extraction reagent and contact between the extraction solution and the luminescent reagent by the contact mechanism.

7. The cell detection device according to claim 1, wherein the processor is further configured to calculate an amount of luminescence derived from the specimen from an amount of luminescence before and after contact between the extraction solution and the luminescent reagent, and determine whether the amount of luminescence derived from the specimen is equal to or more than a certain threshold, thereby determining growth of the cell.

8. The cell detection device according to claim 1, wherein the culture portion, the extraction reagent portion, and the luminescent reagent portion are spaces separated by a first septum and a second septum disposed in the sealed container, and the contact mechanism is a syringe having a syringe needle capable of penetrating the first septum and the second septum.

9. The cell detection device according to claim 1, wherein the culture portion, the extraction reagent portion, and the luminescent reagent portion are spaces separated by a first container holding the culture solution, a second container holding the extraction reagent portion, and a third container holding the luminescent reagent, the first container includes a flow path for dropping the culture solution into the second container, the second container includes a flow path for dropping the extraction solution into the third container, and the contact mechanism has a plunger that controls dropping of the culture solution and a plunger that controls dropping of the extraction solution.

10. The cell detection device according to claim 1, further comprising:

a display that displays a result of determination by the processor.

11. The cell detection device according to claim 1, further comprising:

temperature adjuster that adjusts a temperature of the sealed container.

12. The cell detection device according to claim 1, further comprising:

stirrer that stirs the culture portion.

13. A cell detection method of detecting a cell in a specimen, comprising:

introducing a luminescent reagent into a sealed container;

introducing an extraction reagent to a position separated from the luminescent reagent in the sealed container;

introducing a culture medium to a position separated from the luminescent reagent and the extraction reagent in the sealed container;

adding the specimen to the culture medium to obtain a culture solution;

sealing the sealed container;

bringing a part of the culture solution and the extraction reagent into contact with each other to obtain an extraction solution by moving a contact mechanism to a first position of the sealed container;

bringing the obtained extraction solution and the luminescent reagent into contact with each other to measure an amount of luminescence by moving the contact mechanism to a second position of the sealed container after the first position; and intermittently repeating the obtaining the extraction solution and the bringing the extraction solution and the luminescent reagent into contact with each other to detect growth of the cell in the specimen based on a temporal change in the amount of luminescence.

*    *    *    *    *